US008609027B2

(12) United States Patent
Lee

(10) Patent No.: US 8,609,027 B2
(45) Date of Patent: Dec. 17, 2013

(54) AIR CLEANING FILTER COMPRISING PROTEIN DEACTIVATING AGENT AND PROCESS FOR PRODUCING SAME

(75) Inventor: Sung Hwa Lee, Changwon-si (KR)

(73) Assignee: LG Electronics Inc., Seoul (KR)

( * ) Notice: Subject to any disclaimer, the term of this patent is extended or adjusted under 35 U.S.C. 154(b) by 0 days.

(21) Appl. No.: 13/505,824

(22) PCT Filed: May 4, 2010

(86) PCT No.: PCT/KR2010/002820
§ 371 (c)(1),
(2), (4) Date: May 21, 2012

(87) PCT Pub. No.: WO2011/055893
PCT Pub. Date: May 12, 2011

(65) Prior Publication Data
US 2012/0237406 A1 Sep. 20, 2012

(30) Foreign Application Priority Data
Nov. 3, 2009 (KR) ........................ 10-2009-0105345

(51) Int. Cl.
*A61L 9/00* (2006.01)
(52) U.S. Cl.
USPC .......................................... 422/120; 422/122
(58) Field of Classification Search
USPC .................................................. 422/122, 120
See application file for complete search history.

(56) References Cited

U.S. PATENT DOCUMENTS

| 5,356,555 | A * | 10/1994 | Huth et al. ....................... 422/28 |
| 6,730,144 | B2 * | 5/2004 | Tanaka et al. ................... 95/285 |
| 2002/0192731 | A1* | 12/2002 | Shih ............................ 435/7.92 |
| 2009/0074879 | A1* | 3/2009 | Braguti et al. ................ 424/616 |
| 2009/0133583 | A1 | 5/2009 | Lee et al. ......................... 96/226 |
| 2009/0151571 | A1 | 6/2009 | Lee et al. ......................... 96/226 |

FOREIGN PATENT DOCUMENTS

| EP | 1 510 130 A1 | 3/2005 |
| EP | 1 790 914 A2 | 5/2007 |
| JP | 03-038212 A | 2/1991 |
| JP | 09-117623 A | 5/1997 |
| WO | WO 2007/058475 A2 | 5/2007 |
| WO | WO 2007/058476 | * 5/2007 ............. A01N 63/02 |
| WO | WO 2007/061238 A2 | 5/2007 |

OTHER PUBLICATIONS

Marathe et al. Study of proteinase activity of *Lactobacillus plantarum*. International Journal of Genetics and Molecular Biology vol. 1 (1) pp. 1-5. Apr. 2009.*
Sanchez-Gonzalez et al. Proteolytic processing of dextransucrase of *Leuconostoc mesenteroides*. FEMS Microbiology Letters 181 (1999) Sep. 25-30, 1999.*
Liu et al. THe proteolytic system of lactic acid bacteria revisited: a genomic comparison. BBMC Genomics 11:36. Jan. 2010.*
StrainInfo Beta NRRL B-512 F *Leuconostoc mesenteroides* subsp. mesenteroides retreived Mar. 11, 2013.*
International Search Report dated Aug. 5, 2010 issued in Application No. PCT/KR2010/002820.
European Search Report dated Apr. 4, 2013 issued in Application No. 10 82 8429.0.

* cited by examiner

*Primary Examiner* — Sean E Conley
*Assistant Examiner* — Donald Spamer
(74) *Attorney, Agent, or Firm* — KED & Associates, LLP

(57) ABSTRACT

The present invention relates to an air cleaning filter including a carrier provided therein including a protein deactivating agent coated thereon for removing or sterilizing bacteria, fungi, or virus in the air. The present invention also relates to an air cleaning filter further including kimchi lactic acid bacteria and a disinfectant. The present invention also relates to an air cleaning filter further includes fermented *Ecklonia cava* extract in addition to kimchi lactic acid bacteria and a disinfectant. The air cleaning filter according to the present invention is produced by a method including the step of coating and immobilizing a protein deactivating agent on a carrier, or depending on need, the step of coating and immobilizing a protein deactivating agent, kimchi lactic acid bacteria and a disinfectant on a carrier, or the step of coating and immobilizing a protein deactivating agent, kimchi lactic acid bacteria, a disinfectant and fermented *Ecklonia* cava extract on a carrier. Or, the air cleaning filter of the present invention includes the step of coating a coating solution on the carrier, the coating solution including protein deactivating agent; the protein deactivating agent, kimchi lactic acid bacteria and disinfectant; or the protein deactivating agent, kimchi lactic acid bacteria, disinfectant, fermented *Ecklonia cava* extract, wherein the binder is selected from a group including the silicon modified acryl resin, silicon modified epoxy resin, urethane resin, acryl resin, and silicon resin, and, the step of drying the carrier coated thus, whereby permitting to clean air effectively by removing or sterilizing bacteria, fungi, and virus in the air.

16 Claims, No Drawings

AIR CLEANING FILTER COMPRISING PROTEIN DEACTIVATING AGENT AND PROCESS FOR PRODUCING SAME

TECHNICAL FIELD

The present invention relates to an air cleaning filter comprising a protein deactivating agent, and more particularly the present invention relates to an air cleaning filter which comprises a carrier coated with a protein deactivating agent for making effective removal or sterilization of microbes, such as bacteria, fungi, and virus in the air, and a process for producing the same. Or, alternatively, the present invention relates to an air cleaning filter which comprises a carrier coated with a protein deactivating agent, kimchi lactic acid bacteria and disinfectant; or kimchi lactic acid bacteria, disinfectant and fermented *Ecklonia cava* extract, and a process for producing the same.

BACKGROUND ART

Currently, as interest in the environment is increasing, demand for cleaning the room air is also increasing. Consequently, various air cleaning devices for removing contaminants in the air have been developed and are under development. An air cleaning filter devices uses an air cleaning filter which is required to be in various shapes and have various characteristics according to the types of the removing objects; the sizes of the removing objects; and the characteristics of the removing objects, and thus, a variety of filters are under development.

Especially, an air cleaning filter is required to have antimicroorganism or bactericidal capability for adequate removal or disinfection of microbes, such as bacteria, fungi, and virus floating in the air in order to obtain a satisfactory air cleaning effect.

On the other hand, it has been studied that the virus, a micro life which can not survive for itself but requires a host essentially, infects the host cell, parasitizes at the host, and reproduces itself according to its genetic information in a large amount. That means that the virus is different from other lives and has either a DNA or RNA at a nucleic acid in a cell. The typical examples of RNA viruses are an influenza virus, Ebola virus, AIDS virus, and so on. Since it is known that the RNA viruses make mutation 100,000 to 10,000,000 times easier than the DNA viruses, the prophylaxis of the infection of these RNA viruses is very difficult. Particularly, the influenza A (H1N1) virus, generally called as 'a new kind of influenza,' has a new H1N1 type genome structure different from an existing epidemic influenza virus because it is, for example, born a new kind of virus of swine influenza due to a human influenza virus adapted to a swine host and mixed with an already existing swine influenza virus.

If the new kind of influenza virus would be combined with an avian influenza virus in the swine host by means of gene swapping and thus generate another new kind of virus, then the global infection could be caused by it. It is, also, reported that a human being could also be infected with the above new kind of virus, and even a human being to a human being infection would be very easy, too.

In order to replicate or proliferate, the virus is required to be released from the host cell in viral life cycle (in viral shedding step), and an enzyme called as neuraminidase promotes viral shedding. Therefore, the virus can be sterilized by deactivating the enzyme (neuraminidase) so that prevent the virus from shedding/proliferating.

Meanwhile, it also has been studied that a Korean traditional food kimchi, prepared from many kinds of materials, enables to maintain a balance of nutrients. Kimchi is also known for its antibacterial activity, anti-inflammatory, and even anti-cancerous activity, since it comprises many kinds of antibiotics including allicin and a large amount of lactic acid bacteria influencing to metabolic activity of intestinal flora.

Moreover, according to the result of recent studies, since the culture solution extract of kimchi lactic acid bacteria is effective for treatment of viral disease, such as an avian influenza and a new kind of influenza A (H1N1 virus), interest in Koreans traditional food kimchi become higher and higher. It is known that kimchi has useful efficacy, such as anti-mutation, and anti-cancerous activity due to the functions of the kimchi materials, such as white cabbage and radish; and many kinds of lactic acid bacteria involved in fermentation of the kimchi in combination, and recently, it is also known that kimchi has antiviral activity against an avian influenza virus and a new kind of influenza virus, too.

DISCLOSURE OF INVENTION

Technical Problem

An object of the present invention is to provide an air cleaning filter comprising a carrier coated with a coating solution comprising a protein deactivating agent; a protein deactivating agent, kimchi lactic acid bacteria and a disinfectant; or kimchi lactic acid bacteria, a disinfectant and fermented *Ecklonia cava* extracts for removal or sterilization of microbes, such as bacteria, fungi, and virus in the air.

Another object of the present invention is to provide a process for producing an air cleaning filter comprising a carrier coated with a coating solution comprising a protein deactivating agent; a protein deactivating agent, kimchi lactic acid bacteria and a disinfectant; or kimchi lactic acid bacteria, a disinfectant and fermented *Ecklonia cava* extract for removal or sterilization of microbes, such as bacteria, fungi, and virus in the air.

Solution to Problem

To achieve these objects and other advantages and in accordance with the purpose of the invention, as embodied and broadly described herein, an air cleaning filter comprises a carrier coated with a coating solution comprising a protein deactivating for removing or sterilizing bacteria, fungi, or virus in the air.

Alternatively, the coating solution of the carrier in the air cleaning filter further includes kimchi lactic acid bacteria and a disinfectant. Or, alternatively, the coating solution of the carrier in the air cleaning filter further includes fermented *Ecklonia cava* extract.

In another aspect of the present invention, a process for producing an air cleaning filter comprising a carrier coated with a coating solution comprising a protein deactivating agent includes the step of coating and immobilizing a protein deactivating agent on a carrier.

Alternatively, a process for producing an air cleaning filter comprising a carrier coated with a coating solution comprising a protein deactivating agent, kimchi lactic acid bacteria and a disinfectant includes the step of coating and immobilizing a protein deactivating agent, kimchi lactic acid bacteria and a disinfectant on a carrier. Or, alternatively, a process for producing an air cleaning filter comprising a carrier coated with a coating solution comprising a protein deactivating agent, kimchi lactic acid bacteria, a disinfectant and a fermented *Ecklonia cava* extract includes the step of coating and immobilizing a protein deactivating agent, kimchi lactic acid bacteria, a disinfectant and a fermented *Ecklonia cava* extract on a carrier.

Alternatively, the process for producing an air cleaning filter according to the present invention includes the step of coating a coating solution on the carrier, the coating solution including the protein deactivating agent, and, optionally, kimchi lactic acid bacteria and a disinfectant, or kimchi lactic acid bacteria, a disinfectant, fermented *Ecklonia cava* extract, and a binder, wherein the binder is selected from a group including silicon modified acryl resin, silicon modified epoxy resin, urethane resin, acryl resin, and silicon resin; and the step of drying the carrier coated thus.

As a material of the carrier in the air cleaning filter of the present invention, as far as the material carries out its role of air cleaning, any one can be used regardless of kinds, shapes, sizes, and producing methods, without any limitation. For an example, glass fiber, such as ion exchange fiber, cellulose fiber, asbestos fiber; various kinds of organic fibers; and various kinds of inorganic fiber can be used. Also, metal, such as zinc, copper, aluminum; or even plastic can be used. These materials can be used for various purposes according to the properties of the materials.

A shape of the carrier used in the air cleaning filter according to the present invention can also be modified appropriately, such as a honey comb shape, a granule shape, a net shape, a filter paper shape, a cotton shape, a mesh shape, a plate shape, a foam shape, and the like, according to the air cleaning devices to which the carrier is applied, without particular limitation.

The air cleaning filter according to the present invention can be used as, or together with, deodorant filter, such as an activated charcoal filter used in domestic appliance, such as a refrigerator and air conditioner, HEPA (high efficiency particulate air) filter, and a filter in an air cleaner of a car.

The protein deactivating agent used in the present invention is a mixture of proteinase and metal ion or metal particle.

The proteinase can be anything as far as known as a proteinase regardless of kinds, such as *Bacillus licheniformis* protease, *Bacillus polymyxa* protease, chymotrypsin, Ficin, Papain, Proteinase K, *Streptomyces* protease, Subtilisin A, Trypsin, and the like. Or, the above enzyme of biomass producing the same can be extracted or a commercially available for use and any state of above enzymes can be used without particular limitation. Preferably, Subtilisin A is used.

As the metal ion or metal particle in the protein deactivating agent any metal can be used, regardless of kinds, such as Ca, Mn and Zn, of any state whether it is in ion state or particle state, alone or as a mixture of two or more than two. Preferably, a mixture of Ca and Mn is used.

The protein deactivating agent of the present invention may be a mixture of, for an example, a 70 v % to 50 v % of metal sol having Mn ion and Ca ion mixed at a ratio of 1:1 and a 30 v % to 50 v % of a Subtilisin A solution.

Kimchi lactic acid bacteria used in the present invention may be extracted from kimchi directly, or commercially available without any limitation, regardless of state. For an example, kimchi lactic acid bacteria can be in the state of any one selected from a group of a Kimchi lactic acid bacteria culture solution, a concentration of the culture solution, an extract of the culture solution, a dried culture solution thereof, and a mixture thereof.

Preferably, kimchi lactic acid bacteria can be any one selected from a group including *Leuconostoc* genus Kimchi lactic acid bacteria, *Lactobacillus* genus Kimchi lactic acid bacteria, *Weissella* genus Kimchi lactic acid bacteria and a mixture thereof. It is particularly preferable that Kimchi lactic acid bacteria are *Leuconostoc* genus. It is preferable that *Leuconostoc* genus Kimchi lactic acid bacteria are any one selected from a group including *Leuconostoc citreum, Leuconostoc lactis, Leuconostoc mesenteroides* subsp. *dextranicum, Leuconostoc mesenteroides* subsp. *Mesenteroides, Leuconostoc argentinum, Leuconostoc carnosum, Leuconostoc gellidum, Leuconostoc kimchii, Leuconostoc inhae, Leuconostoc gasicomitatum*, and a mixture thereof. It is preferable that the *Lactobacillus* genus Kimchi lactic acid bacteria are any one selected from a group including *Lactobacillus brevis, Lactobacillus acidophilus, Lactobacillus bulgaricus, Lactobacillus plantarum, Lactobacillus kimchii, Lactobacillus plantarum, Lactobacillus curvatus* subsp. *curvatus, Lactobacillus sakei* sibsp. *sakei* and a mixture thereof. It is also preferable that the *Weissella* genus Kimchi lactic acid bacteria are any one selected from *Weissella koreensis, Weissella hanii, Weissella kimchii, Weissella soli, Weissella confuse*, and a mixture thereof.

It is preferable that kimchi lactic acid bacteria used in the present invention are in a form of a lactic acid bacteria culture extract.

As disinfectant used in the present invention having antibacterial, antifungal and antiviral activity, any form and/or kind of disinfectant can be used without particular limitation as far as disinfectant is harmless to a human body. It is preferable that disinfectant is any one selected from a group including sodium desoxycholate, glutaraldehyde and quaternary ammonium, and more preferably, glutaraldehyde. Sodium desoxycholate has an effect in which sodium desoxycholate gives influences to a cell membrane to suppress cell growth, and glutaraldehyde has an effect in which glutaraldehyde connects between proteins to set enzymes, thereby making activity of the protein poor. Quarternary ammonium raises pH, and thus, makes a living condition of the bacteria unfavorable.

The air cleaning filter according to the present invention further includes fermented *Ecklonia cava* extract. Fermented *Ecklonia cava* extract includes dieckol component of a phlorotannin group which has an excellent antibacterial/anti-inflammatory activity and has been used for a long time. In the present invention, after mixing *Ecklonia cava* and distilled water, the mixture is pulverized with a homogenizer, sterilized by a steam high pressure sterilizer at 121° C. for 15 minutes, left at a room temperature until cooled down, and fermented in a shake culture at 30° C. Then, methanol is added to the *Ecklonia cava* fermented thus, stirred and extracted in a mantle for 3 hours for three times repeatedly, filtered, and concentrated under vacuum in a 60° C. isothermal water tank with a rotary vacuum vaporizer, and an extract component thereof is vaporized to the maximum, to obtain the fermented *Ecklonia cava* extract powder.

The air cleaning filter of the present invention can be produced by including the step of spraying a solution (coating solution) to a carrier or dipping the carrier in the coating solution including the protein deactivating agent, and, optionally, kimchi lactic acid bacteria and disinfectant, or kimchi lactic acid bacteria, disinfectant, fermented *Ecklonia cava* extract, and a binder selected from a group including silicon modified acryl resin, silicon modified epoxy resin, urethane resin, acryl resin, and silicon resin. Optionally, the coating solution can further include metal. The metal can be Ag, Cu and Zn, and can be used individually, or as mixture thereof, preferably with about 1 v % to 5 v %.

The air cleaning filter according to the present invention can be produced by coating a protein deactivating agent, and, optionally, kimchi lactic acid bacteria and disinfectant, or kimchi lactic acid bacteria, disinfectant, a fermented *Ecklonia cava* extract on a carrier directly. Or, The air cleaning filter according to the present invention can be produced by coating a coating solution on a carrier by spraying or dipping after preparing the coating solution including the protein deactivating agent, kimchi lactic acid bacteria and disinfectant, or kimchi lactic acid bacteria, disinfectant, and fermented *Ecklonia cava* extract. The step of coating and immobilizing the protein deactivating agent, and optionally kimchi lactic acid bacteria and disinfectant, or kimchi lactic acid bacteria, disinfectant, and fermented *Ecklonia cava* extract on a carrier in the air cleaning filter can be performed by a method known in this field of art. Depending on cases, it is required to change the protein deactivating agent, and optionally kimchi lactic acid bacteria and disinfectant, or kimchi lactic acid bacteria, disinfectant, and fermented *Ecklonia cava* extract to a state suitable for coating depending on properties of the carrier. In order to immobilize the protein deactivating agent, and optionally kimchi lactic acid bacteria and disinfectant, or kimchi lactic acid bacteria, disinfectant, and fermented *Ecklonia cava* extract on the carrier, an immobilizing technology suitable for the purpose of use can be used by means of a chemical or physical method.

In another method for producing an air cleaning filter in which the protein deactivating agent; and optionally kimchi lactic acid bacteria and disinfectant, or kimchi lactic acid bacteria, disinfectant; and fermented *Ecklonia cava* extract is coated on a carrier, a coating solution is prepared by mixing the protein deactivating agent, and optionally kimchi lactic acid bacteria and disinfectant, or kimchi lactic acid bacteria, disinfectant, and fermented *Ecklonia cava* extract with a binder, such as silicon modified acryl resin, silicon modified epoxy resin, urethane resin, acryl resin, and silicon resin, and the coating solution prepared thus is coated on a surface of the carrier in an air cleaning filter by spraying or dipping. There is no particular limitation in the method for preparing the coating solution as far as the protein deactivating agent; and optionally kimchi lactic acid bacteria and disinfectant, or kimchi lactic acid bacteria, disinfectant, and fermented *Ecklonia cava* extract can be mixed with the binder enough to be coated on the surface of the carrier. It is preferable that a coating solution consists of 0.5 v % to 10 v % of the protein deactivating agent, 3 v % to 10 v % of kimchi lactic acid bacteria, 0.05 v % to 3 v % of disinfectant, 0.5 v % to 10 v % of fermented *Ecklonia cava* extract, and 85 v % to 95 v % of the binder and water in view of coating and mixing. In this instance, the 85 v % to 95 v % of the binder and water has 20 v % to 30 v % of the binder and 70 v % to 80 v % of the water. In above composition, if a ratio thereof is too high, coating is difficult, and if too low, a performance can be poor. Depending on cases, metal may be further added. The metal can be Ag, Cu and Zn, and can be used individually, or mixed with, and the amount of the metal can be about 1 v % to 5 v % in the composition.

In the producing method of the present invention, before the step for coating with kimchi lactic acid bacteria, disinfectant, and fermented *Ecklonia cava* extract and the like on a carrier, the step for washing the carrier to be used with appropriate washing water or drying the carrier washed thus by heat treatment can be added. Depending on cases, it is preferable that oil stuck to a surface of the carrier of metal during production or storage is removed therefrom. In a case the carrier is dried, a drying period and temperature can be adjusted according to a shape, a kind and a size of the carrier to be used. Moreover, after coating kimchi lactic acid bacteria, disinfectant, and fermented *Ecklonia cava* extract on the carrier, the step for drying the carrier coated thus can be included.

The air cleaning filter produced according to the present invention is cut to a required size for use as the air cleaning filter of an air cleaning device. The air cleaning filter produced according to the present invention can be used, not only individually within the same product, but also together with a related art air cleaning filter, deodoring filter, and the like. Thus, the air cleaning filter of the present invention can be used widely, in domestic or office air cleaning filters where the air cleaning filter is required, and in automobiles, refrigerators, air conditioners, and other domestic appliances.

Advantageous Effects of Invention

The present invention has following advantageous effects.
The air cleaning filter according to the present invention including a protein deactivating agent coated thereon can effectively clean up microbes, such as bacteria, fungi, and virus in the air by disinfecting and sterilizing the microbes. Especially, the air cleaning filter according to the present invention can provide a safe and efficacious antiviral effect against the avian flu virus, the human influenza virus, and the new kind of influenza virus.

BEST MODE FOR CARRYING OUT THE INVENTION

Reference will now be made in detail to the specific embodiments of the present invention, examples of which are illustrated in the accompanying drawings. Wherever possible, the same reference numbers will be used throughout the drawings to refer to the same or like parts.

1. Production of an Air Cleaning Filter

After preparing a metal sol with Mn ions and Ca ions at a ratio of 1:1, 60 v % of the metal sol and 40 v % of a Subtilisin A solution are mixed to prepare a protein deactivating agent. After mixing 30 g of *Ecklonia cava* and 600 ml of distilled water, the mixture is pulverized with a homogenizer, sterilized by a steam high pressure sterilizer at 121° C. for 15 minutes, left at a room temperature until cooled down, and fermented for 3 days in a shake culture at 30° C. Then, 6 liters of methanol is added to the *Ecklonia cava* fermented thus, stirred and extracted in a mantle for 3 hours for three times repeatedly, filtered, and concentrated under vacuum in a 60° C. isothermal water tank with a rotary vacuum vaporizer, and an extract component thereof is vaporized to the maximum, to obtain 24 g of fermented *Ecklonia cava* extract powder.

Coating solutions are prepared each to include the protein deactivating agent; fermented *Ecklonia cava* extract; *Leuconostoc citreum*, which is kimchi lactic acid bacteria culture solution extract commercially available; glutaraldehyde; metal in which Ag, Cu, and Zn form a metal sol at a ratio of 1:1:2; silicone modified epoxy resin binder comprising 10% epoxy resin and 90% silicone resin; and distilled water, according to sets of the composition in the following table 1.

Units in the table 1 are v %.

TABLE 1

| Embodiment | 1* | 2* | 3* | 4* | metal | binder | Distilled water |
|---|---|---|---|---|---|---|---|
| 1 | 2 | — | — | — | 3 | 20 | 75 |
| 2 | 2 | 5 | 0.2 | — | 3 | 25 | 64.8 |
| 3 | 2 | 5 | 0.2 | 2 | 3 | 25 | 62.8 |

TABLE 1-continued

| Embodiment | 1* | 2* | 3* | 4* | metal | binder | Distilled water |
|---|---|---|---|---|---|---|---|

1* Protein deactivating agent
2* Kimchi lactic acid bacteria culture solution extract
3* Glutaraldehyde
4* Fermented Ecklonia cava extract A Jabra type filters of an electrostatic non woven fabric is dipped in each of the coating solutions of above sets of the composition for two minutes, respectively. The filters dipped thus are removed from the coating solutions left at a room temperature for 30 to 60 minutes (to let the coating solutions flow down), and dried at 70° C. for 60 minutes to fabricate filter samples, respectively.

2. An Antibacterial Test of the Filter Against *Staphylococcus aureus*

(1) Preparation of a Test Piece

A pre-incubated *S. aureus* solution ($10^9$ cfu/ml) is diluted and inoculated to a 100 ml of sterilized neural solution (0.2% culture broth, 0.5% NaCl) in a conical flask so as to be $10^5$ cfu/ml.

30 test samples each with 1.0×1.0 cm square are prepared, and the obtained neutral solution above is placed in the test samples. These are called as anti-bacteria processed test pieces.

30 filters without any anti-bacteria process step are provided with sizes the same with the test samples, respectively, and placed in 100 ml of the neutral solution above in order to provide the control group.

As the control group, after diluting a flask prepared by using a physiological salt solution and shaking well, 1 ml of the obtained solution is taken and an initial number of bacteria is counted by a mixed dilution plating incubation method (pour plate).

The filter and the conical flask inoculated the bacteria therein are shaken and contacted at 35° C. shaking incubator at 150 rpm for 24 hours.

After contacted with the filter for 24 hours, the obtained culture medium with the bacteria are diluted by ten-fold serial dilution, 1 ml of the obtained solution is taken, placed in a sterilized plate and incubated in a mixed dilution plate by using nutrient agar.

The bacterial plate are incubated at an 37° C. incubator for 18 to 24 hours.

(2) Test Result

After 24 hours, the colonies of the bacteria are counted and the following table 2 shows a result of the count.

TABLE 2

| | | Time (hours) | |
|---|---|---|---|
| | | 0 | 24 |
| control | No. of bacteria | $2.2 \times 10^4$ | $1.1 \times 10^9$ |
| | Reduction ratio | | |
| Embodiment 1 | No. of bacteria | $2.2 \times 10^4$ | $3.4 \times 10^2$ |
| | Reduction ratio | | 99.9% |
| Embodiment 2 | No. of bacteria | $2.2 \times 10^4$ | Not detected |
| | Reduction ratio | | 99.9% |
| Embodiment 3 | No. of bacteria | $2.2 \times 10^4$ | Not detected |
| | Reduction ratio | | 99.9% |

Table 2 shows the antibacterial performance on *S. aureus* in the examples.

3. Anti-Fungus Rate Test of the Filters on *Aspergillus niger*

In order to determine an antifungal effect of the filters, anti-fungus rate tests are performed for the filters of embodiments 1 to 3 according to JIS Z 2911 (Antifungal test method).

As a result of the tests, embodiment 1 shows "1," embodiment 2 shows "0" and embodiment 3 shows "1." In this instance, "0" denotes no mycelia growth, "1" denotes mycelia growth being less than ⅓ of an entire area, and "2" denotes mycelia growth being more than ⅓ of an entire area.

4. Antiviral Test (Shaking Flask Method) of the filters on *Feline calicivirus* (FCV)

(1) Preparation of a Test Piece 6 test samples are provided, each with a size of 1.0×1.0 cm square, and placed on maintenance media (2% FBS (Fetal Bovine Serum), DMEM (Dulbeco's Modified Eagle's Medium)).

FCV diluted to about $10^5$ TCID$_{50}$/ml is inoculated to the test samples, and reacted at a room temperature each time.

When the reaction is finished, the virus is diluted at maintenance media (2% FBS, DMEM) in 10 fold serial dilution.

After removing a growth medium by using an aspirator in a 96 well-plate of single film, the obtained diluted virus is inoculated to 8 wells each by 25 μl.

After adsorbing the virus in 5% $CO_2$ incubator for 90 minutes at 37° C., 100 ml of maintenance medium is added to each of the wells.

A potency of the virus is determined by calculating TCID$_{50}$ (tissue culture infectious dose 50) measured from CrFK (Crandel feline kidney) cells compared an amount of the virus left after reaction with the extract for a predetermined time period with the control group.

(2) Result of Test

After visualizing cells dissolved by the virus on a fifth day of virus culture, dilution stage of the well showing more than 50% of CPE is calculated by Reed-Munch method and expressed with Log TCID$_{50}$. The following table 3 shows a result of the calculation.

TABLE 3

| | | Time (hours) | | |
|---|---|---|---|---|
| | | 5 | 8 | 10 |
| control group | | $5.01.0 \times 10^5$ | $4.53.2 \times 10^4$ | $3.51.1 \times 10^9$ |
| Embodiment 1 | TCID$_{50}$ | $2.01.0 \times 10^2$ | $2.01.0 \times 10^2$ | — |
| | Reduction rate | 99.9% | 99.9% | 99.9% |
| Embodiment 2 | TCID$_{50}$ | $2.01.0 \times 10^2$ | — | — |
| | Reduction rate | 99.9% | 99.9% | 99.9% |
| Embodiment 3 | TCID$_{50}$ | $1.53.2 \times 10$ | — | — |
| | Reduction rate | 99.9% | 99.9% | 99.9% |

Table 3 shows antiviral performance on FCV.

As a result of the tests, all of the embodiments shows the excellent antiviral performances according to the present invention, and especially, the antiviral effect is more excellent in the embodiment including the protein deactivating agent, kimchi lactic acid bacteria culture solution extract, disinfectant, and fermented *Ecklonia cava* extract.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

INDUSTRIAL APPLICABILITY

The air cleaning filter comprising a protein deactivating agent coated thereon according to the present invention can clean up microbes, such as bacteria, fungi, and virus in the air by sterilizing the microbes, and can provide a safe and effective antiviral effect against the virus that causes the bird flu, the human influenza virus, and the new kind of influenza virus.

The invention claimed is:

1. An air cleaning filter comprising:

a carrier coated with a coating solution comprising a protein deactivating agent for removing or sterilizing bacteria, fungi, or virus in the air, wherein the coating solution further includes kimchi lactic acid bacteria and a disinfectant, and wherein the coating solution further includes fermented *Ecklonia cava* extract.

2. The air cleaning filter as claimed in claim 1, wherein the protein deactivating agent is a mixture of a proteinase and metal.

3. The air cleaning filter as claimed in claim 2, wherein the proteinase is one of Subtilisin A, *Bacillus polymyxa* protease, or Proteinase K.

4. The air cleaning filter as claimed in claim 2, wherein the mental is the state of metal ion or metal particle and wherein the mental is one of Ca, Mn, Zn or a mixture thereof.

5. The air cleaning filter as claimed in claim 1, wherein kimchi lactic acid bacteria is in the form of a Kimchi lactic acid bacteria culture solution, a concentration of the culture solution, an extract of the culture solution, a dried culture solution thereof, or a mixture thereof.

6. The air cleaning filter as claimed in claim 1, wherein disinfectant is any one of sodium desoxycholate, glutaraldehyde or quaternary ammonium.

7. A method for producing an air cleaning filter of the claim 1 comprising the step of coating and immobilizing a protein deactivating agent on a carrier.

8. A method for producing an air cleaning filter of the claim 1 comprising the step of coating and immobilizing a protein deactivating agent, kimchi lactic acid bacteria and a disinfectant on a carrier.

9. A method for producing an air cleaning filter of the claim 1 comprising the step of coating and immobilizing a protein deactivating agent, kimchi lactic acid bacteria, a disinfectant and fermented *Ecklonia cava* extract on a carrier.

10. The method as claimed in claim 7, wherein the step of coating and immobilizing the protein deactivating agent; the protein deactivating agent, kimchi lactic acid bacteria and a disinfectant; or the protein deactivating agent, kimchi lactic acid bacteria, a disinfectant and fermented *Ecklonia cava* extract on a carrier includes the step of coating a coating solution including the protein deactivating agent; the protein deactivating agent, kimchi lactic acid bacteria and a disinfectant; or a protein deactivating agent, kimchi lactic acid bacteria, a disinfectant, fermented *Ecklonia cava* extract, and a binder on the carrier, wherein the binder is a silicon modified acryl resin, silicon modified epoxy resin, urethane resin, acryl resin, or silicon resin, and the step of drying the carrier coated thus.

11. The method as claimed in claim 7, wherein the protein deactivating agent is a mixture of a proteinase and metal.

12. The method as claimed in claim 11, wherein the proteinase is one of Subtilisin A, *Bacillus polymyxa* protease, or Proteinase K.

13. The method as claimed in claim 11, wherein the metal is the state of metal ion or metal particle, and wherein the metal is one of Ca, Mn, or Zn, or a mixture thereof.

14. The method as claimed in claim 8, wherein kimchi lactic acid bacteria is in the form of Kimchi lactic acid bacteria culture solution, a concentration of the culture solution, an extract of the culture solution, a dried culture solution thereof, or a mixture thereof.

15. The method as claimed in claim 8, wherein a disinfectant is one of sodium desoxycholate, glutaraldehyde or quaternary ammonium.

16. The method as claimed in claim 10, wherein the coating solution further includes metal.

* * * * *